(12) United States Patent
Lindström et al.

(10) Patent No.: US 7,237,946 B2
(45) Date of Patent: Jul. 3, 2007

(54) USE OF IR CAMERA

(75) Inventors: Kjell Lindström, Gäddö (SE);
Christoph König, Frankfurt (DE)

(73) Assignee: FLIR Systems AB, Danderyd (SE)

( * ) Notice: Subject to any disclaimer, the term of this patent is extended or adjusted under 35 U.S.C. 154(b) by 170 days.

(21) Appl. No.: 10/972,470

(22) Filed: Oct. 26, 2004

(65) Prior Publication Data
US 2005/0089076 A1 Apr. 28, 2005

(30) Foreign Application Priority Data
Oct. 28, 2003 (SE) ................... 0302837

(51) Int. Cl.
*G01N 25/00* (2006.01)
*G01J 5/00* (2006.01)

(52) U.S. Cl. .................... 374/16; 374/28; 374/121

(58) Field of Classification Search ............. 374/16, 374/28
See application file for complete search history.

(56) References Cited

U.S. PATENT DOCUMENTS

| | | | |
|---|---|---|---|
| 5,281,815 A * | 1/1994 | Even-Tov | 250/339.04 |
| 2005/0115873 A1 * | 6/2005 | de Villers et al. | 209/518 |
| 2007/0034798 A1 * | 2/2007 | Hamrelius et al. | 250/332 |

FOREIGN PATENT DOCUMENTS

| | | | |
|---|---|---|---|
| JP | 61-134652 | | 6/1986 |
| JP | 01224654 A | * | 9/1989 |
| JP | 2-114161 | | 4/1990 |
| JP | 6-118040 | | 4/1994 |
| JP | 6-326903 | | 11/1994 |
| JP | 08184555 A | * | 7/1996 |
| JP | 9-37230 | | 2/1997 |
| JP | 2003315156 A | * | 11/2003 |

* cited by examiner

*Primary Examiner*—Diego Gutierrez
*Assistant Examiner*—Mirellys Jagan
(74) *Attorney, Agent, or Firm*—Young & Thompson

(57) ABSTRACT

The inventive IR camera is used to identify areas of a surface in which there is an increased risk of condensation, by
  imaging the surface
  determining, from humidity and temperature values, a condensation temperature at which there is a risk of condensation on the surface,
  comparing the temperature in at least one image point registered by the camera to the condensation temperature
  coloring any image points having a temperature lower than the condensation temperature in a particular color, or grey tone, selected to indicate an increased risk of condensation.

5 Claims, 1 Drawing Sheet

USE OF IR CAMERA

TECHNICAL FIELD

The present invention relates to a method for identifying areas on a surface that have an increased risk of condensation and an IR camera.

BACKGROUND AND PRIOR ART

In many applications, in particular when inspecting buildings, there is a need to be able to determine the specific points or areas where there is an increased risk of condensation. Such condensation increases the risk of damage due to damp. Prior art methods for such inspections include conductivity measurements. Conductivity sensors usually measure the conductivity in one particular point and are therefore limited to rather small areas. To make a time-efficient inspection, therefore, areas that are assumed to have an increased risk are selected by the person carrying out the measurements. There is thus a risk that high-risk areas are missed, and/or the measurements may be time-consuming.

Further, such inspections often involve imaging in places that are hard to access, such as high up, underneath a machine or a piece of furniture, or around corners, so that the operator is forced to stretch or bend or assume another uncomfortable or risky position.

OBJECT OF THE INVENTION

It is therefore an object of the present invention to enable inspection of large areas with respect to the risk of condensation, in an efficient way with a reliable result.

SUMMARY OF THE INVENTION

This object is achieved according to the invention by a method of determining at least one area of a surface in which there is an increased risk of condensation, comprising the steps of
- using an IR camera to create an image of the temperature distribution in at least a part of the surface
- entering at least one value for the relative air humidity and at least one value for the air temperature in air surrounding the surface,
- determining, on the basis of the entered humidity and temperature values at least one condensation temperature at which there is a risk of condensation on the surface,
- comparing the temperature in at least one image point of the image to the condensation temperature
- colouring any image points having a temperature lower than the condensation temperature in a particular colour, or grey tone, selected to indicate an increased risk of condensation.

The object is also achieved according to the invention by the use of an IR camera to identify areas of a surface in which there is an increased risk of condensation, comprising:
imaging the surface to create an image of the temperature distribution in at least a part of the surface;
entering at least one air temperature value and at least one air humidity value for the air temperature and relative humidity, respectively, near the surface
determining, on the basis of the entered humidity and temperature values at least a first condensation temperature at which there is a risk of condensation on the surface,
comparing the temperature in at least one image point of the image to the condensation temperature
colouring any image points having a temperature lower than the condensation temperature in a particular colour, or grey tone, selected to indicate an increased risk of condensation.

The object is also achieved by an IR camera comprising focusing means for focusing incoming IR radiation from an object in the IR camera to generate a signal corresponding to the incoming IR radiation, to be passed to a signal conditioning unit for signal conditioning, said IR camera comprising
means for receiving information about at least one air temperature value and at least one air humidity value for the air temperature and relative humidity, respectively, near the surface,
means for calculating, on the basis of the entered humidity and temperature values at least one condensation temperature at which there is a risk of condensation on the surface,
means for comparing the temperature in at least one image point of the image to the condensation temperature,
means for modifying the image in such a way that image points indicating a lower temperature than the condensation temperature are coloured in a particular colour, or grey tone, selected to identify areas of the surface having an increased risk of condensation.

The invention is based on the fact that the condensation on a surface is dependent on the atmospheric humidity, the air temperature and the temperature of the surface. Condensation is also dependent on atmospheric pressure, which may however be seen as neglectable in state of the art calculations.

The following equation may be used to calculate the dewpoint temperature Td (see Corey Simon, Dewpoint and Wetbulb Temperature, November 2000:

$$Td = \frac{116.9 + 237.3\ln(p)}{16.78 - \ln(p)} \quad (1)$$

where p is the ambient vapour pressure in kPa.

$$p = \frac{RH}{100} \cdot 0.611 \cdot e^{(17.27T/T+237.3)} \quad (2)$$

where RH is the relative humidity and T is the temperature.

In this way an operator can identify immediately in the whole registered image, any areas having an increased risk of condensation. The use of an IR camera in this context enables larger areas to be inspected at once.

According to a first embodiment, the step of entering at least one value for the relative air humidity and at least one value for the air temperature in air surrounding the surface is performed manually.

In this case the air temperature and humidity may be measured separately. Alternatively, this method can be used for simulating different conditions, by imaging the surface using different values for the air temperature and/or humidity.

Alternatively, the step of entering at least one value for the relative air humidity and at least one value for the air temperature in air surrounding the surface comprises measuring the relative air humidity and air temperature in air surrounding the surface using an air temperature sensor and an air humidity sensor, said sensors being arranged to communicate the values to the camera. In this embodiment the IR camera further comprises:

means for receiving a first and a second air humidity value, means for calculating a first and a second condensation temperature corresponding to the first and second air humidity value, respectively, and means for colouring any areas of the surface having a temperature between the first and the second condensation temperature in a particular colour, or grey tone.

According to a preferred embodiment a first and a second air humidity value are entered and a first and a second condensation temperature is calculated, corresponding to the first and second air humidity value, respectively. Any image point having a temperature between the first and the second condensation temperature is then coloured in a particular colour, or grey tone. In this embodiment the IR camera includes means for receiving a first and a second air humidity value, means for calculating a first and a second condensation temperature corresponding to the first and second air humidity value, respectively, and means for colouring any areas of the surface having a temperature between the first and the second condensation temperature in a particular colour, or grey tone.

In this case a range in the surface temperature, corresponding to areas that have an increased risk of condensation at the selected air temperature, can be seen if the relative air humidity is between the two or more entered values, for example, between 30% and 40%, between 40% and 50%, etc.

The method can also comprise the step of entering a first and a second air temperature value and calculating a first and a second condensation temperature corresponding to the first and second air temperature value, respectively, and colouring any image point having a temperature between the first and the second condensation temperature in a particular colour, or grey tone. The IR camera then includes means for entering a first and a second air temperature value, means calculating a first and a second condensation temperature corresponding to the first and second air temperature value, respectively, and means for colouring any areas of the surface having a temperature between the first and the second condensation temperature in a particular colour, or grey tone.

In this case areas will be indicated that have an increased risk of condensation at the selected relative humidity, if the air temperature is between the two or more entered values, for example, between 20 and 30 degrees, between 30 and 40 degrees, etc.

The method may also comprise entering a value for the atmospheric pressure and determining the at least one condensation temperature on the basis of the entered humidity, temperature and atmospheric pressure values. In this case the IR camera comprises means for receiving information about an atmospheric pressure and means for calculating the at least one condensation temperature on the basis of the entered humidity, temperature and atmospheric pressure values.

BRIEF DESCRIPTION OF THE DRAWINGS

In the following the invention will be described in more detail, by way of embodiments with reference to the appended drawings, in which.

DETAILED DESCRIPTION OF EMBODIMENTS

Figure 1:
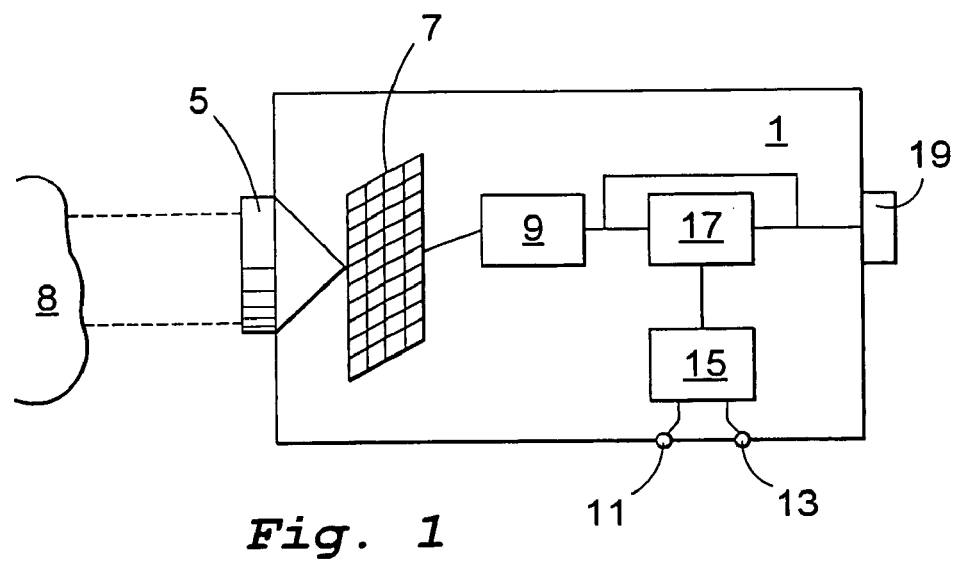
FIG. 1 shows an IR camera according to a first embodiment of the invention.

FIG. 1 shows an IR camera according to the invention. For registering IR images the camera unit 1 comprises the same functions as prior art cameras. The gathering of data and the data processing performed prior to displaying the image are carried out in the conventional way. This technology is known to the skilled person, but will be briefly discussed in the following. The incoming radiation to the camera is focused by at least one lens 5 onto a detector array 7. The detector array is typically a matrix of detector elements, each detecting radiation from a corresponding area on an object 8 being imaged. From the detector array the signal is fed to a signal conditioning unit 9 which performs conventional signal conditioning such as corrections for the inherent offset and gain drift.

It should be noted that the IR camera does not necessarily comprise a focal plane array. The inventive concept can also be implemented in an IR camera using an IR scanner.

According to the invention, the IR camera also comprises temperature input means 11 for receiving from a temperature sensor information about the temperature in the air surrounding the object, and humidity input means 13 for receiving from a humidity sensor information about the atmospheric humidity in the air surrounding the object 8. The temperature input means 11 and the humidity input means 13 may be adapted for wired or wireless communication with the respective sensors. Alternatively, information about the air temperature and humidity may be measured separately and input to the camera in another way, e.g. manually. The information about the air temperature and humidity is forwarded to a temperature calculation unit 15 arranged to calculate, on the basis of the air temperature and humidity information, a calculated condensation temperature, or dew point temperature, at which humidity will condense on the surface of the object, thus increasing the risk of condensation, which may lead to damage due to damp.

If desired, the atmospheric pressure can also be taken into account.

From the signal conditioning unit 9 the registered image of the object 8 passes to a colour adjusting unit 17 arranged to compare the measured temperature in each point of the image of the object 8 to the calculated temperature and, identify image points in which the measured temperature is lower than the calculated temperature. The colour adjusting unit 17 also changes the colour of all such points to a particular colour, or shade of grey, which has been preselected to indicate areas where condensation will occur. The image is then displayed to the viewer in a viewfinder and/or a display 19, in a conventional way. It can also be stored, in the camera or outside the camera in ways common in the art.

The calculated condensation temperature may be increased or decreased by a certain factor to include more or fewer points among those considered to have an increased risk of damage due to damp. This security margin may be included automatically in the camera, or may be selectable by the operator.

Of course, the division of the functions performed in units 9, 15 and 17 is merely done to illustrate the functions of the camera. In reality they may be performed in one or two, or more units in, or even outside of, the camera 1. Preferably, as indicated in FIG. 1 by a solid line directly from the signal conditioning unit 9 to the viewer, the modification of the image may be bypassed so that a conventional IR image is shown on the display 19 of the IR camera.

Figure 2:
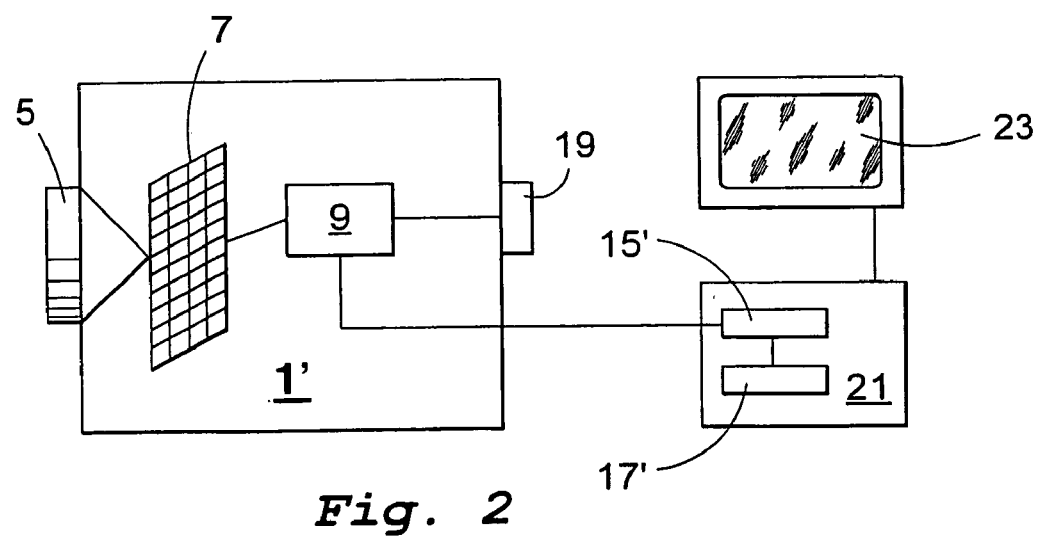
FIG. 2 shows an arrangement according to a second embodiment of the invention.

Alternatively, the camera can be a conventional IR camera 1' as shown in FIG. 2, arranged to output a temperature dependent image of the object. As before, incoming IR radiation from the object is focused by a focusing system 5 onto a focal plane array 7 or onto the scanning device, depending on the type of IR camera used. The signal from the focal plane array 7 (or scanning device) is fed to a signal conditioning unit 9. The output image from the signal conditioning unit 9 can then be transferred to a computer 21, as is well known in the art. The information about the air temperature and atmospheric humidity may be registered by sensors and stored in the camera or may be entered into the computer manually. The computer then comprises units 15', 17' corresponding to the temperature calculation unit 15 and the colour adjusting unit 17 of FIG. 1. The adjusted image, indicating in a particular colour the areas where condensation will occur, can then be displayed on the computer screen 23.

The invention claimed is:

1. An IR camera comprising:
   focusing means for focusing incoming IR radiation from an object in the IR camera to generate image signals corresponding to the incoming IR radiation, to be passed to a signal conditioning unit for signal conditioning,
   means for receiving information about at least one air temperature value and at least one air humidity value for the air temperature and air relative humidity, respectively, near a surface of the object,
   means for calculating, on the basis of the received information about the air humidity and temperature values, at least one condensation temperature at which there is a risk of condensation on the surface,
   means for comparing the temperature in at least one image point of the image signals to the condensation temperature, and
   means for modifying the image signals in such a way that image points indicating a lower temperature than the condensation temperature are highlighted to identify areas of the surface having an increased risk of condensation.

2. An IR camera according to claim 1, further comprising a temperature sensor for providing the at least one air temperture value, and an air humidity sensor for providing the at least one air humidity value.

3. An IR camera according to claim 1, wherein said means for receiving receives first and second air humidity values,
   wherein said means for calculating calculates first and second condensation temperatures corresponding to the first and second air humidity values respectively, and
   wherein said means for modifying highlights areas of the surface having a temperature between the first and the second condensation temperatures.

4. An IR camera according to claim 1, wherein said means for receiving receives first and second air temperature values,
   wherein said means for calculating calculates first and second condensation temperatures corresponding to the first and second air temperature values respectively, and
   wherein said means for modifying highlights areas of the surface having a temperature between the first and the second condensation temperatures.

5. An IR camera according to claim 1, further comprising,
   means for receiving information about an atmospheric pressure, and
   wherein said means for calculating calculates the at least one condensation temperature also on the basis of the received information about the atmospheric pressure.

* * * * *